(12) United States Patent
Nikolaev et al.

(10) Patent No.: US 8,287,712 B2
(45) Date of Patent: Oct. 16, 2012

(54) STATIONARY SEPARATION SYSTEM FOR MIXTURE COMPONENTS

(75) Inventors: Evgenij Nikolaev, Moscow (RU); Jochen Franzen, Bremen (DE)

(73) Assignee: Bruker Daltonik GmbH, Bremen (DE)

( * ) Notice: Subject to any disclaimer, the term of this patent is extended or adjusted under 35 U.S.C. 154(b) by 1501 days.

(21) Appl. No.: 11/534,252

(22) Filed: Sep. 22, 2006

(65) Prior Publication Data

US 2007/0068817 A1    Mar. 29, 2007

(30) Foreign Application Priority Data

Sep. 29, 2005   (DE) .......................... 10 2005 046 657

(51) Int. Cl.
*G01N 27/447* (2006.01)
(52) U.S. Cl. .................. 204/608; 204/600; 204/609
(58) Field of Classification Search .................. 204/450, 204/600, 547, 454, 643, 608, 609
See application file for complete search history.

(56) References Cited

U.S. PATENT DOCUMENTS

| | | | |
|---|---|---|---|
| 5,846,396 A * | 12/1998 | Zanzucchi et al. | 506/33 |
| 7,156,970 B2 * | 1/2007 | Lean et al. | 204/547 |
| 2002/0195342 A1 | 12/2002 | Lee et al. | |
| 2006/0289341 A1 * | 12/2006 | Muller et al. | 209/210 |

FOREIGN PATENT DOCUMENTS

| | | |
|---|---|---|
| DE | 197 09 752 C1 | 3/1999 |
| DE | 693 23 488 T2 | 6/1999 |
| DE | 697 12 348 T2 | 12/2002 |
| EP | 0 376 611 A2 | 7/1990 |
| EP | 0 646 040 B1 | 10/1993 |
| EP | 0 925 115 B1 | 3/1998 |
| GB | 2 266 153 A | 10/1993 |
| WO | WO 02/26292 A1 | 4/2002 |

\* cited by examiner

*Primary Examiner* — Alex Noguerola
*Assistant Examiner* — Gurpreet Kaur
(74) *Attorney, Agent, or Firm* — Law Offices of Paul E. Kudirka

(57) ABSTRACT

Components of a mixture are separated by feeding charged molecules of the components into a end surface of a suitable medium, for example a gel. The molecules are drawn in a first direction through the medium by means of an DC electric field, while at the same time being subjected to an alternating voltage with a strongly asymmetric profile in a direction transverse to the first direction. The nonlinear behavior of the electrically-generated migration causes a large number of molecules to migrate transversely out of the medium while only a small number of molecules reach the opposite end surface of the medium. A superimposed DC voltage in the transverse direction selects which of the mixture components migrate all the way through the medium in the first direction. The separated components can be sampled from the opposite end surface and from points on the upper and lower medium surfaces.

10 Claims, 3 Drawing Sheets

STATIONARY SEPARATION SYSTEM FOR MIXTURE COMPONENTS

FIELD OF THE INVENTION

The invention relates to the separation of the components of mixtures in small volumes, particularly to the separation of proteins or peptides in mixtures for analytical purposes.

BACKGROUND

For analytical purposes, the components of a substance mixture can be separated by gas chromatography (GC), liquid chromatography (HPLC), thin-layer chromatography (TLC), capillary electrophoresis (CE), polyacrylamide gel electrophoresis (PAGE), ion mobility spectrometry (IMS) and other, similar methods. It is specific to all these methods that, in each case, only a small amount of the substance mixture is introduced, and that different migration rates occur for the various components of the mixture, leading to a spatial and/or temporal separation of the components. The individual components leave the respective system in the form of small substance batches ("peaks"), or they are available at the end of the separation process in the form of small local accumulations ("spots" or "bands"). So this is by no means a stationary separation process with constant infeed of mixture at one point and constant sampling of a mixture component at another point. Therefore, none of these methods can be adjusted to the sample quantity by varying the duration, and they cannot collect components of low concentration for enrichment.

There are very few separation systems for mixtures which operate as stationary systems. Most of them can be found in big industry, column distillation being one such example. For analytical micro-preparations, hardly any stationary separation systems are known.

Only in the field of ion mobility has a separation system become known which has stationary operation. The system in question is a "High-Field Asymmetric Waveform Ion Mobility Spectrometer" (FAIMS). If a high alternating voltage is interposed between two concentric tubes, an asymmetric alternating field is formed. In this field, ions introduced migrate to one of the two usually tubular electrodes by virtue of the nonlinear components of their mobility. By superimposing a DC voltage it is now possible to create an equilibrium for precisely one ion species so that precisely this ion species is collected in the space between the two tubes. The ions can be introduced into the system at one point as a mixture and sampled at another point as a separated ion species. The disadvantage here is that the separation system is one which can only be operated as an ion filter: one ion species gets through, but all other ion species are destroyed at the electrodes. A further disadvantage is that there is no active transport of the ion species selected from the infeed point to the sampling point.

The ion mobility at an electric field intensity E obeys the simple law v=K×E, where v is the speed of the ion migration. K is a constant which is a function of the friction cross section of the ions and is thus specific to one ion species. K is called the mobility of the ion species. In general, the mobility K is not independent of the field intensity E, however; and the speed v is thus not simply proportional to the field intensity. On the contrary, the relationship here is:

$$K(E)=K0\times(1+K1\times E2+K2\times E4+\ldots)$$

Here, K0 is the mobility for vanishingly small electric fields. This dependence of the mobility on the field intensity E means that an ion species subjected to an asymmetric alternating voltage migrates in the direction of the field, even though the temporal integral over the voltage profile of the alternating voltage is exactly zero. An asymmetric alternating voltage in this sense is a voltage which has a high voltage maximum toward one side, toward the positive side, for example, but only for a short time, while toward the other side, here toward the negative side, there is only a low voltage but one which lasts much longer. If the constants K1 and K2 are not zero, this asymmetry brings about a migration in one of the two field directions.

It has not been clarified with certainty why the mobility K is a function of the electric field intensity. One hypothesis is that there are variable states of the solvate envelopes around the individual ions, which are always present even in the gaseous state, said envelopes being able to be more or less skimmed off by collisions with ambient gas or friction with the ambient liquid if the migration rate is high. This then changes the cross section, and hence the mobility. For ion mobility spectrometry, it is known that several water molecules are always to be found on the ions, and that these water molecules are subject to a very rapid and constant interchange.

It could also be another type of conformity change of the ions, however. If the molecule has a dipole in addition to its charge then this dipole can be pulled apart in the field. At a high field intensity, the molecule thus becomes longer and thinner, its cross section changes and thus its mobility in the ambient medium. Further mechanisms for conformity changes are conceivable.

The conformity change does not have to occur immediately, it can also have a settling time. To utilize this conformity change for the separation of substances, however, it is always necessary to let the conformity change occur so that it is also detectable, or even to wait until an equilibrium has been reached. This requirement means there is an upper limit for the frequency of the asymmetric alternating field.

Therefore, it is one object of the invention is to provide a stationary separation system for analytical samples. The separation system will preferably also be able to operate in multichannel mode. The separation system will also be suitable for use especially with protein or peptide mixtures. Many mixtures, including peptides and proteins, contain predominantly charged molecules in aqueous solution; the charge averaged over the molecules of a peptide and over time is dependent on the pH value of the solution. The number of charges of a molecule in solution is not an integer, as is the case with gaseous ions, but is only a time average over a continuously oscillating process of ionization and deionization.

SUMMARY

The invention makes the charged molecules of the mixture components migrate through a suitable medium (for example a gel) in one direction (the "drawing direction") by means of an electric DC drawing field, while at the same time subjecting the migrating molecules to an alternating voltage with a strongly asymmetric profile at right angles to the drawing direction. The nonlinear behavior of the electrically generated migration causes a large number of mixture components to migrate transversely out of the medium while only a small number of components migrate parallel to the electric DC drawing field without deflection and can be sampled opposite the infeed point. By superimposing a DC voltage in the transverse direction which compensates for the migration of one component in the transverse direction, it is possible to select which of the mixture components migrate all the way through the medium without deflection. The separated components can be sampled at the end of the drawing direction.

The invention therefore consists in exploiting the nonlinear mobility of charged substance components subjected to electric fields in suitable media in a particular way. The medium can be a gas which is stationary or has laminar motion as in usual ion mobility spectrometers. The gas here must be enveloped in some way. The charge of the substance molecules must then to be specially generated by ionization. It is also possible to move molecules dissociated in solution, i.e., in any form of molecular ions, through a liquid or, particularly favorably, through a gel. In this case, the ionic form of the molecules does not have to be produced specially. In principle, the degree of dissociation, and hence the temporal-spatial average of the charge per molecule, can be easily adjusted via the pH value of the solution. In this invention, however, the solution should have a high resistance to maintain the electric field within the solution without breakdown. Peptides, proteins and most other biomolecules should be solved in distilled water, as known from PAGE electrophoresis.

Even the permeability of many substances through rubbery solids can be exploited if it is possible to produce ionic forms of the molecules here. This migration of the substances in solution through liquid, gelatinous or rubbery media is very similar to the mobility of ions in gases; the migration in the liquid or in the gel is just a great deal slower.

The medium can have various forms, for example the form of an elongated, not too thin layer or a flat rectangular plate. The thickness of the layer or plate does not have to be uniform, for example, and the layer does not have to be level. One of the directions at right angles to the drawing direction is here considered to be the transverse direction. If gases or liquids act as the medium, they should be held together by rigid envelopes or vessels and kept resting in one place or in calm laminar flow. If the medium is a gel, it can keep its own shape in small dimensions; for larger forms it requires suitable support.

In the invention, the molecules of the mixture components are continuously introduced at a small point of the medium, for example at one end of a flat layer. The mixture components are now drawn through the medium by an electric drawing field, as is the case with PAGE, for example. The drawing field can be constant over time, or it can be modulated or pulsed. At the same time, an alternating voltage with a strongly asymmetric profile is applied to the medium in the transverse direction, preferably with a transverse DC field of adjustable field intensity superimposed. The nonlinear behavior of the electrically generated migration means that a large number of mixture components migrate transversely out of the medium while only a small number of components in equilibrium between asymmetric alternating field and superimposed transverse DC field migrate in a straight line and reach the opposite surface of the medium, for example the opposite end surface. If a transverse DC voltage is superimposed, it can be used to select which of the mixture components migrates all the way through the medium in the drawing direction. This mixture component can be sampled continuously at the arrival point by a flowing liquid or can be collected over a prolonged period in a resting liquid. In this embodiment the device acts as a filter; only the substances reaching the arrival point are sampled and processed further. For good utilization of the nonlinear mobility, the field intensity in the transverse direction should be much larger than the intensity of the drawing field.

Instead of the asymmetric alternating voltage, the migration can occur by means of a DC field applied in a transverse direction which changes asymmetrically in direction and intensity from location to location along the drawing direction, but which is constant over time. The asymmetry here consists in the fact that the migration is over a short migration path in the longitudinal direction, over which there is a high field in a transverse direction, then a low field in the opposite transverse direction, over a longer migration path in the longitudinal direction.

By means of a large number of sampling points on the surface of the medium, the substances migrating out of the medium in a transverse direction can be collected in a large number of individual fractions and processed further. In this embodiment, the separation is a multichannel separation. The fractions can be collected in a large number of small liquid volumes or also directly deposited by some sort of adsorption on an analytical sample support.

The electric drawing and transverse fields can be generated, for instance, by a large number of parallel, linearly extended straight or curved electrodes arranged in two layers with the medium enclosed between them. The layers of electrodes can be mounted on surfaces of the medium or in the vicinity of the surfaces. The electrodes can also each be combined with small sampling channels. The electric drawing and transverse fields can also be generated by two continuous resistive layers at opposite sides of the medium.

BRIEF DESCRIPTION OF THE DRAWINGS

FIG. 5 represents the case of an electric drawing field of constant strength, which results in straight migration paths. In FIG. 6, by contrast, the electric drawing field strength is initially very strong on the inlet side and becomes much weaker toward the opposite end surface. This results in curved migration paths and, depending on the composition of the mixture, a possibly better distribution of the substances over the sampling channels.

DETAILED DESCRIPTION

While the invention has been shown and described with reference to a number of embodiments thereof, it will be recognized by those skilled in the art that various changes in form and detail may be made herein without departing from the spirit and scope of the invention as defined by the appended claims.

Figure 3:
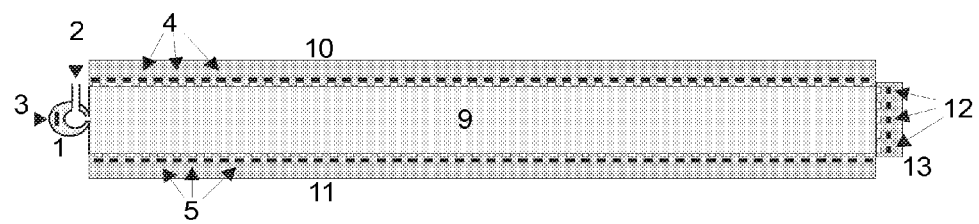
FIG. 3 shows a multichannel separation device in which the gel (9) is covered both above and below by a plastic parts (10) and (11) which contains a series of fine sampling channels for the removal of separated components, each channel adjacent to one of the series of electrodes within the layers (4) and (5). At the end surface on the sampling side there are also several sampling channels in another plastics part (13), each reinforced with electrodes (12), whose voltages can draw the charged molecules out of the gel (9) and into the sampling channels.
Figure 4:
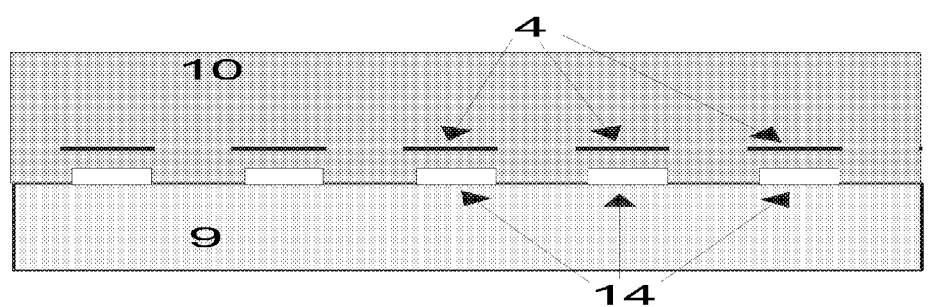
FIG. 4 is a section of FIG. 3, showing The small more clearly the fine channels or grooves of the striated pattern (14), each in the vicinity of an electrode from the electrode layer (4).

A first favorable embodiment is shown in FIGS. 3 and 4. It is for a separation in a gel (9) which is not too thin. The gel (9) in the form of a rectangular plate is located between two plastic shells (10) and (11) which firmly envelope the gel and give it support. The gel is about ten centimeters long, four centimeters wide and one centimeter thick. On the upper and lower surfaces of the gel (9), always close to the electrodes of the two electrode layers (4) and (5), the plastic shells (10) and (11) have a large number of small transverse grooves (14), each around half a millimeter deep and approx. one millimeter wide which, when filled with liquid, preferably slightly acidified water, can serve as sampling channels when the device is in operation. The grooves (14) run parallel to the end surfaces of the gel. At the base of the grooves (14) are the individual electrodes of the two electrode layers (4) and (5), insulated from each other and from the liquid channels, for the generation of both the electric drawing fields and also the transverse fields. The inner surfaces of the grooves (14) are made strongly hydrophilic using familiar methods so that no mixture components can become firmly deposited here as a result of hydrophobic-hydrophobic interactions.

At the end of the gel (9) on the inlet side is the infeed device (1) for the solution with the peptide mixture, which serves here as an example of a substance separation. The infeed device (1) brings the solution with the peptide mixture in direct contact with the end of the gel (9) by a narrow, elongated aperture, about one millimeter wide and twenty millimeters long. The elongated aperture is parallel to the surface of the gel plate. An electrode (3) close to the internal channel of the infeed device ensures that the charged peptide molecules migrate out of the liquid and into the gel under the effect of the electric field. The solution with the peptide mixture can be fed to the infeed device through two tubular channels (2); a circuit is also possible. Here also the internal surfaces have been made strongly hydrophilic in order not to lose hydrophobic substances through surface adsorption.

From isoelectric electrophoresis, it is known that the majority of peptides in solution are charged, the strength of the charge being dependent on the pH value of the solution. The peptides are also charged in the gel, the strength of the charge again varying with the pH value of the liquid in the gel. So even in their native state, the peptides (or proteins) can be drawn through the gel with the aid of an electric field. But the peptides can also be derivatized by special measures in a familiar way with charge-carrying chemical groups in order to increase their charge in solution.

The electrodes of the two electrode layers (4) and (5), which are here embedded into the plastic shells (10) and (11), can have rigid connecting wires to make contact (not shown in FIG. 3), which protrude out of the plastic shells (10) and (11). These connecting wires can be connected very simply via plug-on flat ribbon cable connectors to flat ribbon cables which lead to suitable electronic circuit boards for the power supply. It is therefore advisable to select the separations of the individual electrodes in the electrode layer (4) to correspond exactly to the separations of the contact points in standardized flat ribbon cable connectors (1.27 or 2.0 millimeters). The same applies to the individual electrodes of the electrode layer (5), and also to the electrodes (12) in the plastic part (13).

The two electrode layers (4) and (5), each with electrodes which are insulated from each other in the plastic shells (10) and (11) on both sides of the medium, form an electric longitudinal drawing field with a voltage difference of up to a few kilovolts in the gel (9), similar to the voltages at electrode rings around the drift tubes in ion mobility-spectrometry. In this longitudinal drawing field, charged peptides (or other molecules) migrate slowly toward the opposite end surface.

Figure 7:
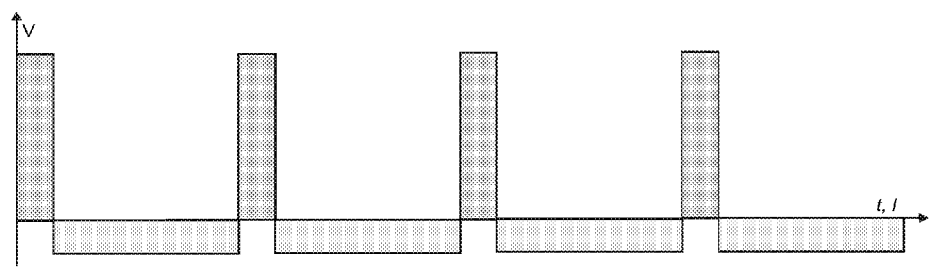
FIG. 7 illustrates an example for the temporal (t) and spatial (l) asymmetric alternating voltage, which brings about the separation of the substance components transverse to the drawing direction.

By means of suitable voltage superimpositions, the electrodes of the two electrode layers (4) and (5) also form the asymmetric transverse alternating field transversely through the layer of the gel (9). An example of a temporal (or local) profile of such asymmetric alternating voltage is shown in FIG. 7. The asymmetric transverse alternating field enables the charged peptides to migrate transverse to the layer toward one of the two electrode layers (4) or (5). The migration rate is specific to each peptide. Since the maximum transverse field intensity should be a multiple of the drawing field intensity, the voltages here should likewise rank up to a few kilovolts. If the thickness of the gel is around one tenth of its length, then for the same voltages, the intensity of the transverse field is around ten times as high as that of the drawing field. The frequency should not be too high. If the medium is a gel, the frequency should be between a few Hertz and a few hundred Hertz, since for every altered voltage in each voltage cycle an equilibrium for the migration rate should again be reached.

Furthermore, there is an adjustable DC difference across the electrodes of the two electrode layers (4) and (5), which forms an electric transverse DC field. This transverse DC field serves to compensate for the migration of a desired component toward one of the electrode layers; this component thus does not migrate out of the gel (9), but runs undisturbed (although in a slight zig-zag motion) toward a point on the opposite end surface, for example to the middle sampling channel at the electrodes (12).

Figure 1:
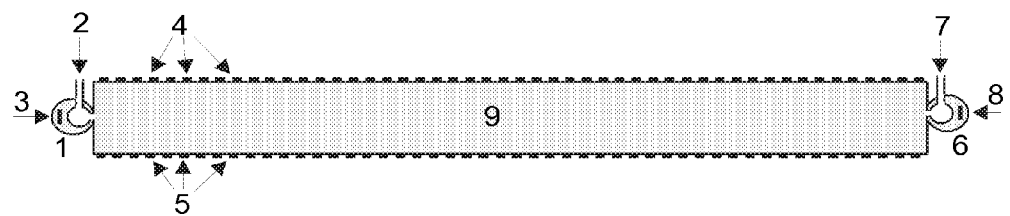
FIG. 1 illustrates the principle of a single-channel, stationary separation device with a gel (9). Charged molecules of a solution which is fed in via the supply (2), can be transferred from the infeed device (1) into the gel (9) by the electrode (3). Voltages across the many parallel individual electrodes of the two electrode layers (4) and (5) can generate the desired DC drawing and transverse asymmetric AC fields in the gel (9). The species of molecule which migrates in a straight line can be drawn out of the gel (9) via the sampling device (6) with the help of the electrode (8) into a solvent and removed through the small tube (7).
Figure 2:
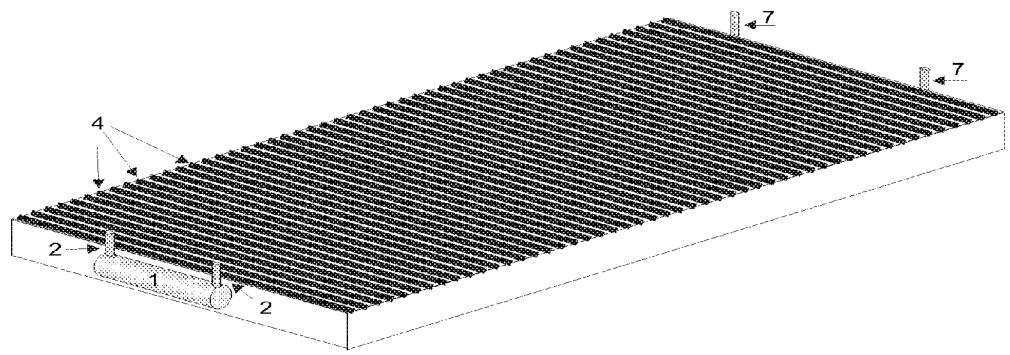
FIG. 2 illustrates the principle of the stationary separation device from FIG. 1 in a perspective view.

The principle of a very simply constructed single-channel embodiment, shown in FIG. 1, has only one single sampling point (6) on the end surface opposite the infeed device (1). The sampling volume can be filled with liquid via tubular connections (7). An electrode (8) draws the charged molecules of the mixture component which arrives here into this liquid; this component can thus be steadily removed, dissolved in the liquid, through the connections (7). Alternatively, the component can be collected over a prolonged period in a resting liquid before it is removed. This separation system has a single channel; only one single selected substance is sampled from the mixture. It could, for example, be a peptide at very low concentration in a complex mixture, which could not be analytically measured without such enrichment. The analytical measurement can relate to the structure of this peptide, to the identity, or only to the precise mass. This single-channel embodiment has the disadvantage that the unused components remain in the gel and have to be specially washed out if the gel is to be used a number of times.

The end surface can also be equipped with several parallel sampling points (12), as can be seen in FIG. 3. This means that several components with only slightly different K1 values can be collected, for example for the comparative measurement of several posttranslational modifications of the same peptide.

Finally, it is also possible to use some or all of the grooves connected with the electrodes of the two electrode layers (4) and (5) for sampling the components which arrive there in each case. This forms a multichannel separation system. The sampling from these many channels can be controlled with a microfluid switching system, for example. The liquids in these channels can also be filled over a prolonged period, only the length of the channel over the width of the gel needing to be filled with liquid. This requires only 10 to 50 microliters of liquid, depending on the form of the grooves and the width of the gel. The liquids can finally be pressed out of the channels via a simple distribution system in the plastic parts (10), (11) and (13) into a microtitre plate, which can accommodate 96 or 384 samples with liquids, for example.

Such a system with many channels is advantageous even it is used analytically as a single-channel separation system because all the non-selected substances can be removed from the gel continuously.

Figure 5:
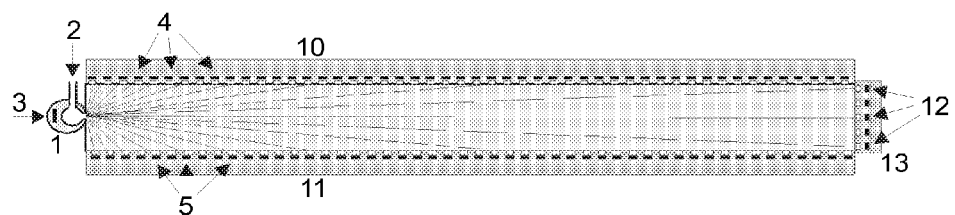
In FIGS. 5 and 6, the migration paths for the charged molecules of various substances have been added.
Figure 6:
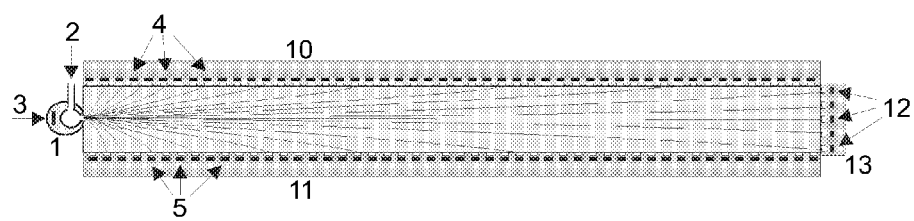

Since all the electrodes of the two electrode layers (4) and (5) can be selected independently of each other, it is possible to change the separation behavior electronically. For example, the electric drawing field strength does not have to be constant; it can start stronger at the substance infeed, for example, in order to generate a higher migration rates in the drawing direction here, as shown in FIG. 5. FIG. 4, in contrast, illustrates the straight migration paths of substances in a constant drawing field. A drawing field which is not constant is favorable if there are many components which already migrate transversely out of the gel after a short migration. These components can thus be spread over more sampling channels.

The asymmetric alternating voltages must not have the same value everywhere, nor the same degree of asymmetry. This, too, allows the components to be spread better and more uniformly over the sampling channels. However, the compensating transverse DC fields must then also be suitably adjusted.

In particular, the electrodes of the two electrode layers (4) and (5) can generate asymmetric transverse fields which are static but locally changing. An example of the voltage profile for this local variation of the fields is illustrated in FIG. 7, where there is now a position axis l instead of a time axis t. The molecules which are drawn through these alternating transverse fields by the drawing field will migrate transversely to the drawing direction, as they would with an asymmetric alternating field. Here again, a DC part of the transverse field can be selected so that a desired component migrates straight ahead. This method, which uses no alternating voltages, is particularly economic because there are no dielectric losses at all.

If, in the embodiment described, the gel (9) between the plastic shells (10) and (11) is omitted and the space between the plastic shells is sealed, one has a device in which gaseous mixtures of ions can be separated in the gaseous medium. It is, however, difficult here to empty the sampling channels without exciting the gas medium to turbulence or uncontrolled motion. It is somewhat simpler to use a liquid, especially when one uses a highly viscous liquid with a high surface tension which does not penetrate into the small sampling channels. In the small sampling channels there can be a second liquid of another liquid phase, into which the charged molecules of the separated components can be drawn by electric fields.

It is somewhat simpler to separate the gases and liquids from the sampling channels by permeable membranes. These membranes can be penetrated electrophoretically or by simple diffusion. Thin membranes made of silicone rubber are suitable for these purposes, for example.

A gel is an open-pored, three-dimensional molecular lattice which is very stable and filled with a liquid, predominantly with water. The pH value of the water can be adjusted by dissolving acids or bases (or suitable salts). Molecules in solution can migrate through this open-pored structure if they are provided with suitable thrust. The molecules, mainly charged molecules, are generally surrounded by a solvate envelope made of liquid molecules. It is possible that the skimming off of parts of the solvate envelope is responsible for the mobility being dependent on the electric field intensity.

Organic molecules, however, can also permeate through certain types of solids (so-called permeable solids), mainly rubber-like solids. It is known that organic molecules of a few hundred atomic mass units can permeate very quickly through silicone rubber membranes. A membrane one millimeter thick is penetrated in less than a second. This permeation without an electric field is based solely on diffusion, but it is assumed that charged molecules can also be moved by electric fields. By dissolving organic acids or bases it is possible to adjust the pH value within the rubber, making it possible to adjust the charge of bio-organic molecules. It is not known whether this electrically assisted permeation has a nonlinear behavior, i.e., whether the proportionality of the permeation rate to the electric field intensity is disturbed. If the permeation rate is not strictly proportional to the field intensity, then this also makes it possible to form a separation system according to this invention.

The substances migrate in the medium along a path which can be straight or curved, depending on the form of the electric fields. The path begins at the device for feeding in the substance mixture. With a punctiform infeed of the substances of the mixture, the paths are initially very fine, but widen by diffusion as the distance from the infeed point increases. The widening occurs in both spatial directions transverse to the direction of migration. This diffusion is basically unavoidable. It is, however, possible to keep the path focused in one of the two transverse directions if the electric transverse field is given a gradient. Such a focusing transverse field can be achieved by two concentric electrode layers, each having the form of cylinder segments. Focusing in the radial direction occurs between these curved electrode layers. This effect can be used to increase the spatial resolution of the components.

By combining several separation devices according to this invention it is also possible to construct very complex separation systems. It is thus possible, for example, to operate several single-channel separation systems in parallel, each separation device being set to a different component. It is then possible to collect the substances which do not migrate to the sampling points and feed them back to the infeed devices. This process can be continued until all the desired components have been extracted sufficiently well from the mixture.

With this system it is also possible to proceed so that the substances which do not migrate to the sampling point of the first separation device are fed to a second separation device where a second component is separated off. More components are removed in further stages. It is thus possible to separate off a series of components in succession.

With knowledge of this invention, it is relatively easy for the specialist in the field to develop suitable separation methods and separation equipment to suit his particular separation tasks.

What is claimed is:

1. A stationary separation system for separating the components of a substance mixture, comprising
   a) a spatially limited medium in which charged molecules of the components can be made to migrate by an electric drawing field,
   b) a device for generating an electric drawing field in the medium along a drawing direction from a medium first side to a medium second side,
   c) a device for generating a temporally asymmetric alternating electric field in a direction transverse to the drawing direction, wherein the asymmetric electric field causes the charged molecules to migrate out of the medium in a direction transverse to the drawing direction,
   d) a device for the infeed of the substance mixture at one point on the medium along the medium first side, and
   e) a device for sampling a component of the substance mixture from another point on the medium along the medium second side.

2. A separation system according to claim 1, further comprising an adjustable electric transverse DC field superimposed on the asymmetric alternating electric field in a direction transverse to the drawing direction.

3. A separation system according to claim 1, comprising a plurality of devices for sampling a plurality of components of the mixture from a plurality of locations on the medium.

4. A separation system according to claim 1, wherein the medium is selected from the group consisting of a gas, a liquid, a gel and a permeable solid.

5. A separation system according to claim 1, comprising two electrode layers with parallel electrodes which are insulated from each other for the generation of both the electric drawing field as well as the transverse fields, the medium being located between the two electrode layers.

6. A separation system according to claim 5, wherein the medium has the form of an elongated rectangular plate, and wherein both the electric drawing field in the longitudinal direction of the rectangular plate as well as the transverse fields are generated by a plurality of linear extended electrodes over the upper and under the lower surfaces of the rectangular plate, the electrodes being arranged parallel to the end surfaces of the rectangular plate.

7. A separation system according to claim 6, wherein the linear extended electrodes are each arranged near sampling channels for the separated components.

8. A separation system according to claim 1, wherein the device for infeeding the substance mixture comprises an electrode, which when a voltage is applied, generates an electric field that presses charged substance molecules into the medium.

9. A separation system according to claim 1, wherein at least one device for sampling a component of the substance mixture is equipped with an electrode that draws the components out of the medium when a voltage is applied.

10. A stationary separation system for separating charged molecules of a substance mixture, comprising
   a spatially limited medium;
   a device for generating an electric drawing field in the medium from a medium first side to a medium second side to cause the charged molecules to migrate through the medium in a drawing direction;
   a device for generating in a direction transverse to the drawing direction an electric DC field that changes asymmetrically in direction and intensity along the drawing direction so that the electric field causes the charged molecules to migrate out of the medium in a direction transverse to the drawing direction;
   a device for the infeed of the substance mixture at one point on the medium first side; and
   a device for sampling a component of the substance mixture from another point on the medium second side.

* * * * *